US009384555B2

(12) United States Patent
Razeto et al.

(10) Patent No.: US 9,384,555 B2
(45) Date of Patent: Jul. 5, 2016

(54) MOTION CORRECTION APPARATUS AND METHOD

(75) Inventors: Marco Razeto, Edinburgh (GB); Sebastian Meller, Edinburgh (GB)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 545 days.

(21) Appl. No.: 13/540,174

(22) Filed: Jul. 2, 2012

(65) Prior Publication Data
US 2014/0003690 A1  Jan. 2, 2014

(51) Int. Cl.
*G06K 9/00* (2006.01)
*G06T 7/00* (2006.01)
*A61B 6/00* (2006.01)
*G06T 7/20* (2006.01)

(52) U.S. Cl.
CPC .......... *G06T 7/0081* (2013.01); *A61B 6/507* (2013.01); *G06T 7/003* (2013.01); *G06T 7/0016* (2013.01); *G06T 7/2006* (2013.01); *G06T 2207/10016* (2013.01); *G06T 2207/30008* (2013.01)

(58) Field of Classification Search
None
See application file for complete search history.

(56) References Cited

U.S. PATENT DOCUMENTS

| 6,718,055 | B1 | 4/2004 | Suri |
| 7,840,050 | B2 | 11/2010 | Ramamurthy et al. |
| 2001/0048757 | A1* | 12/2001 | Oosawa ......................... 382/130 |
| 2003/0215120 | A1* | 11/2003 | Uppaluri ................ A61B 6/482 382/128 |
| 2005/0251021 | A1* | 11/2005 | Kaufman et al. ............ 600/407 |
| 2005/0281373 | A1* | 12/2005 | Both ..................... A61B 5/7264 378/62 |
| 2006/0239585 | A1* | 10/2006 | Valadez et al. ................ 382/275 |
| 2007/0297657 | A1* | 12/2007 | Mattes et al. .................. 382/128 |
| 2010/0235352 | A1* | 9/2010 | Slutsky ................. G06T 7/0012 707/723 |
| 2011/0069906 | A1* | 3/2011 | Park et al. ....................... 382/284 |
| 2012/0172718 | A1* | 7/2012 | Huang et al. ................... 600/425 |
| 2013/0182925 | A1* | 7/2013 | Razeto ..................... A61B 6/03 382/131 |

OTHER PUBLICATIONS

William R. Crum, et al., "Information Theoretic Similarity Measures in Non-Rigid Registration", Information processing in medical imaging, Proceedings of IPMI, Aug. 2003, 11 pages.
Jim Piper, et al., "Objective Evaluation of the Correction by Non-Rigid Registration of Abdominal Organ Motion in Low-Dose 4D Dynamic Contrast-Enhanced CT", Physics in Medicine and Biology, vol. 57, No. 6, Mar. 2012, 19 pages.
Ken Shoemake, et al., "Matrix Animation and Polar Decomposition", Proceedings of Graphical Interface, 1992, 7 pages.

* cited by examiner

*Primary Examiner* — Sumati Lefkowitz
*Assistant Examiner* — Ryan P Potts
(74) *Attorney, Agent, or Firm* — Oblon, McClelland, Maier & Neustadt, L.L.P.

(57) ABSTRACT

An apparatus for providing a motion-corrected time series of image data sets, comprises an image selection unit for obtaining a series of sets of image data, each set of image data representative of a region at a different time, and for automatically determining a sub-region of interest, and a registration unit that is configured to, for each of a plurality of sets of image data in the series, perform a registration, for the sub-region of interest, to register one of a reference data set of the series and the set of image data to the other of that reference data set and the set of image data.

23 Claims, 11 Drawing Sheets

MOTION CORRECTION APPARATUS AND METHOD

FIELD

Embodiments described herein relate generally to a method of, and apparatus for, motion correction of image data, for example time sequences of three-dimensional medical image data.

BACKGROUND

Perfusion studies, in which a contrast agent is injected into a human body or other subject, and allowed to perfuse through regions of interest have become widely used to quantify blood flow through specific organs or tissues. A series of images of the human body or other subject is obtained using one of a variety of medical imaging modalities, for example CT, MRI, PET, or X-ray imaging, and the perfusion of the contrast agent is studied as a function of time.

For example, dynamic CT Perfusion is performed by injecting contrast agent into the blood of a patient, and scanning the patient at a region of interest at certain time intervals using a CT scanner, with the aim of observing and measuring how the blood perfuses in various tissues of that region, especially tumours. In dynamic bone perfusion studies, the main aim is to diagnostically assess regions inside and around diseased bones, including visualization and quantification of tumours.

In the case of tumours, correct visualization and accurate quantification of perfusion can lead to better diagnosis and therapeutic decisions.

Figure 1A:
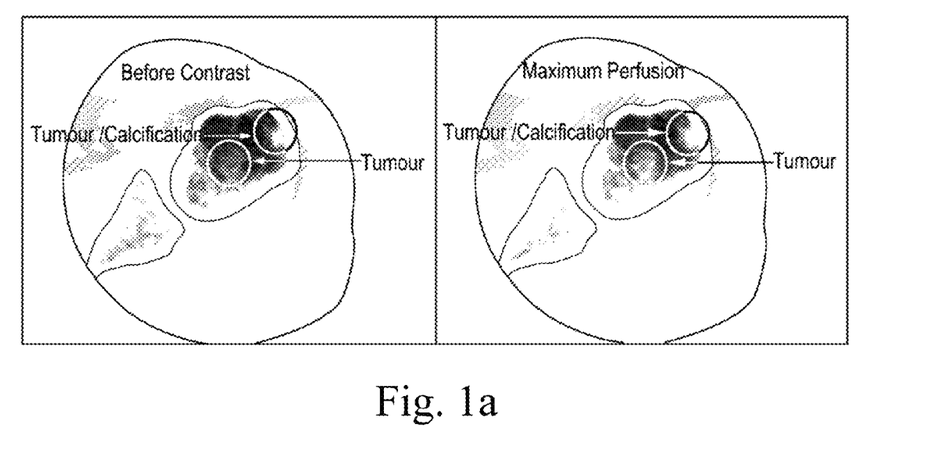
FIGS. 1a and 1b represent line-drawn images and corresponding original scan images of a bone region in the presence of a tumour, before and after perfusion of a contrast agent.
Figure 1B:
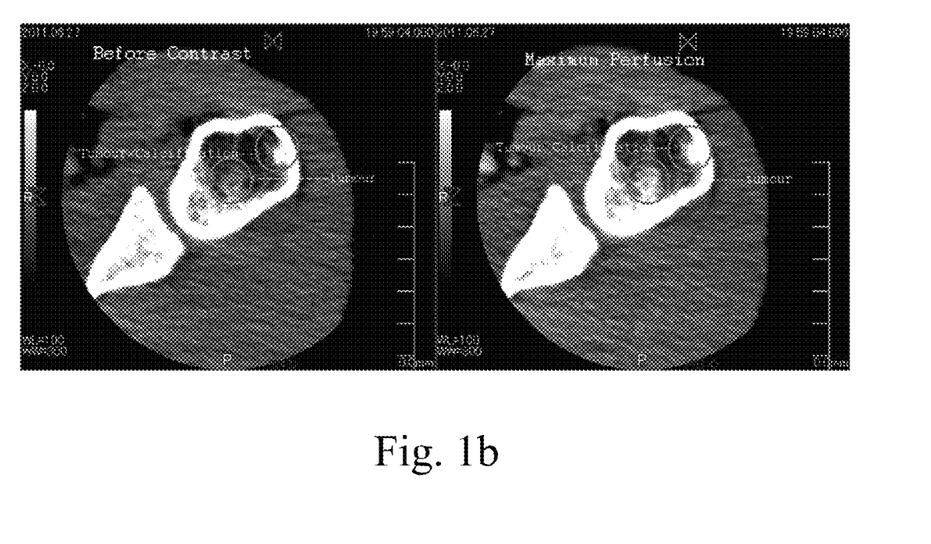

However, accurate quantification of perfusion across a series of time-separated images can be difficult due, for example, to movement of the patient or other subject or, in some cases, the similarity in appearance or intensity of contrast-enhanced tissue and other substances present in the patient or other subject. In the case of CT perfusion studies contrast agent perfusing into bone tumours provides a similar image intensity to the image intensity of bone. As bone tumours are adjacent to or surrounded by bone, it can be difficult to determine accurately the location, boundaries or perfusion characteristics of bone tumours from post-contrast images in CT perfusion studies due to the presence of bone. By way of example, FIG. 1a is a line drawing representing a bone region that includes a tumour, obtained from CT data acquired before injection of contrast agent, and a line drawing of the same region after perfusion of contrast agent into the region. FIG. 1b shows the original scan images from which the line drawings of FIG. 1a were obtained. The presence of the bone makes it more difficult to distinguish the boundaries and properties of the tumour.

Subtraction images, obtained by subtracting pre-contrast image data obtained before the contrast agent had perfused to regions of interest from contrast-enhanced images, may prove useful in better visualizing the pathology, and obtaining more reliable perfusion measurements. However, accurate subtraction requires accurate registration of the data, such that a voxel in one data set represents the same position within the patient or other subject as a corresponding voxel in another data set from which it is to be subtracted.

Perfusion analysis acquisition may be time consuming, increasing the risk of patient movement and thus inaccuracies in image subtraction. Patient movement during the acquisition time causes different parts of the patient's anatomy to be represented by corresponding voxels in the different image data sets of the series, making subtraction difficult.

Manual alignment of different image data sets obtained in perfusion studies is a possible way of resolving this, but is time-consuming, difficult for the operator and error-prone.

It is also known for an operator to manually place regions of interests for measurements at approximately the same anatomical positions in each single image data set of a perfusion study, in order to obtain meaningful anatomy-oriented measurements, but again, this is time-consuming, difficult and error-prone.

BRIEF DESCRIPTION OF THE DRAWINGS

Embodiments are now described, by way of non-limiting example, and are illustrated in the following figures, in which.

DETAILED DESCRIPTION

According to an embodiment there is provided a method of providing a motion-corrected time series of image data sets that comprises obtaining a series of sets of image data, each set of image data representative of a region at a different time. The method further comprises automatically determining a sub-region of interest, and for each of a plurality of sets of image data in the series, performing a registration, for the sub-region of interest, to register one of a reference data set and the set of image data to the other of that reference data set and the set of image data.

Figure 2:
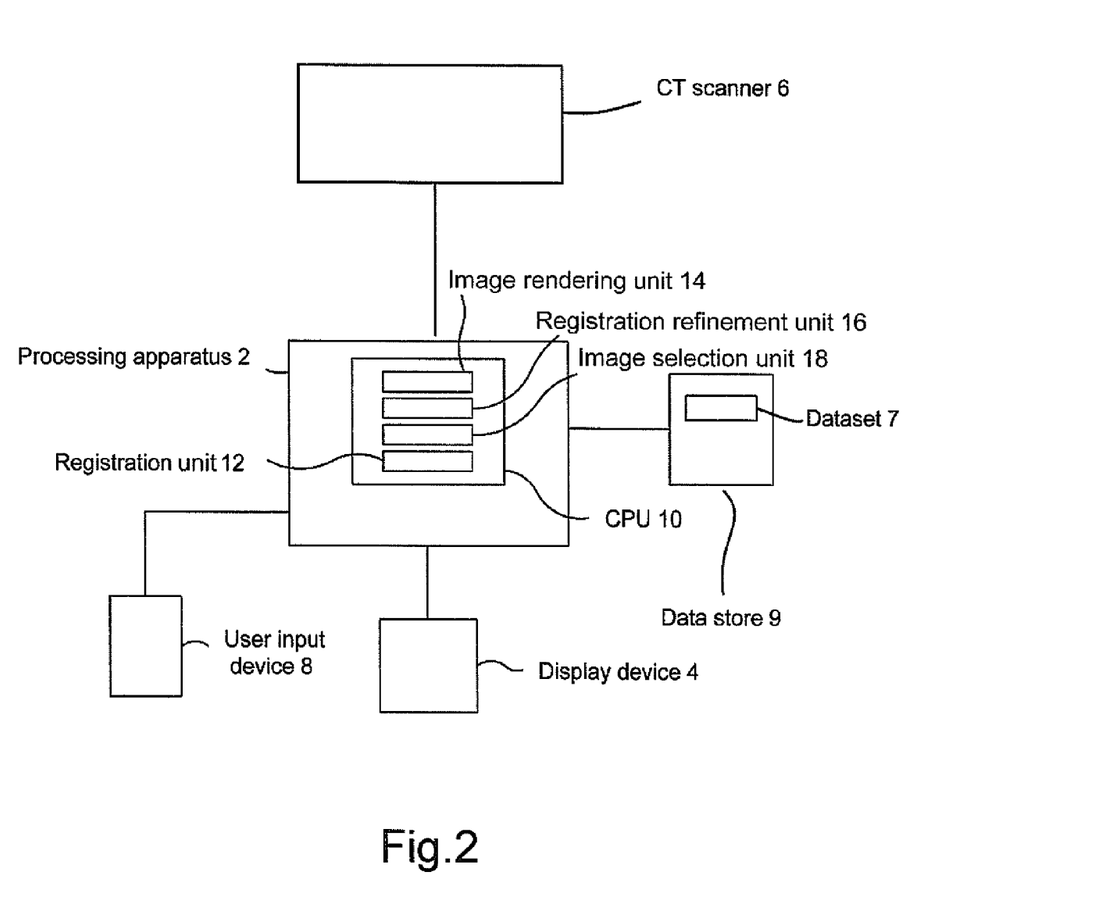
FIG. 2 is a schematic diagram of an image data processing system according to an embodiment.

A medical image processing apparatus according to an embodiment is illustrated schematically in FIG. 2 and is configured to implement the method described in the preceding paragraph. The apparatus comprises a processing apparatus 2, in this case a personal computer (PC) or workstation that is connected to a display device 4, a CT scanner 6 and a user input device or devices 8, in this case a computer keyboard and mouse. The apparatus also includes a data store 9.

Any suitable type of CT scanner may be used that is able to perform three dimensional CT measurements on a patient or, other subject, for example one of the Aquilion® series of scanners produced by Toshiba Medical Systems Corporation. Although the embodiment of FIG. 2 is described in relation to CT scan data, any other suitable type of scanner producing any suitable type of image data may be used in alternative embodiments, for example MR data of suitable form and if subject to suitable pre-processing, digital subtraction X-ray angiography data, PET data, SPECT data, or ultrasound data.

The processing apparatus 2 provides a processing resource for automatically or semi-automatically processing image data, and comprises a central processing unit (CPU) 10 that is operable to load and execute a variety of software modules or other software components that are configured to perform a method as described in detail below with reference to FIG. 3.

The processing apparatus includes a registration unit 12 for performing rigid and non-rigid registration procedures, an image rendering unit 14 for rendering and displaying images, a registration refinement unit 16 for refining registrations, and an image selection unit 18 for selecting sub-regions of interest.

The processing apparatus 2 also includes a hard drive and other components of a PC including RAM, ROM, a data bus, an operating system including various device drivers, and hardware devices including a graphics card. Such components are not shown in FIG. 2 for clarity.

In the embodiment of FIG. 2 the processing apparatus 2 comprises a 2.0 GHz chipset and 2×4 core processors, that provide a multi-threaded environment using 9 threads, and 6.0 Gbytes of RAM is provided. However, any suitable CPU and other components may be used.

In the embodiment of FIG. 2 a series of image data sets 7 is received by the processing apparatus 2 from the CT scanner 6 following performance of scans by the scanner 6, and are stored in the data store 9 and processed by the processing apparatus. Although the scanner 6 shown in the embodiment of FIG. 2 is a CT scanner, any other suitable type of scanner can be used to obtain the image data sets in alternative embodiments.

In a variant of the embodiment of FIG. 2, the processing apparatus 2 receives image data sets from a remote data store (not shown) rather than from the scanner 6. The remote data store stores a large number of different data sets obtained from many different scanners over a period of time together with associated patient data. The data store may be a server that stores a large quantity of patient data, and may form part of a Picture Archiving and Communication System (PACS), for example the Toshiba Rapideye® system.

Figure 3:
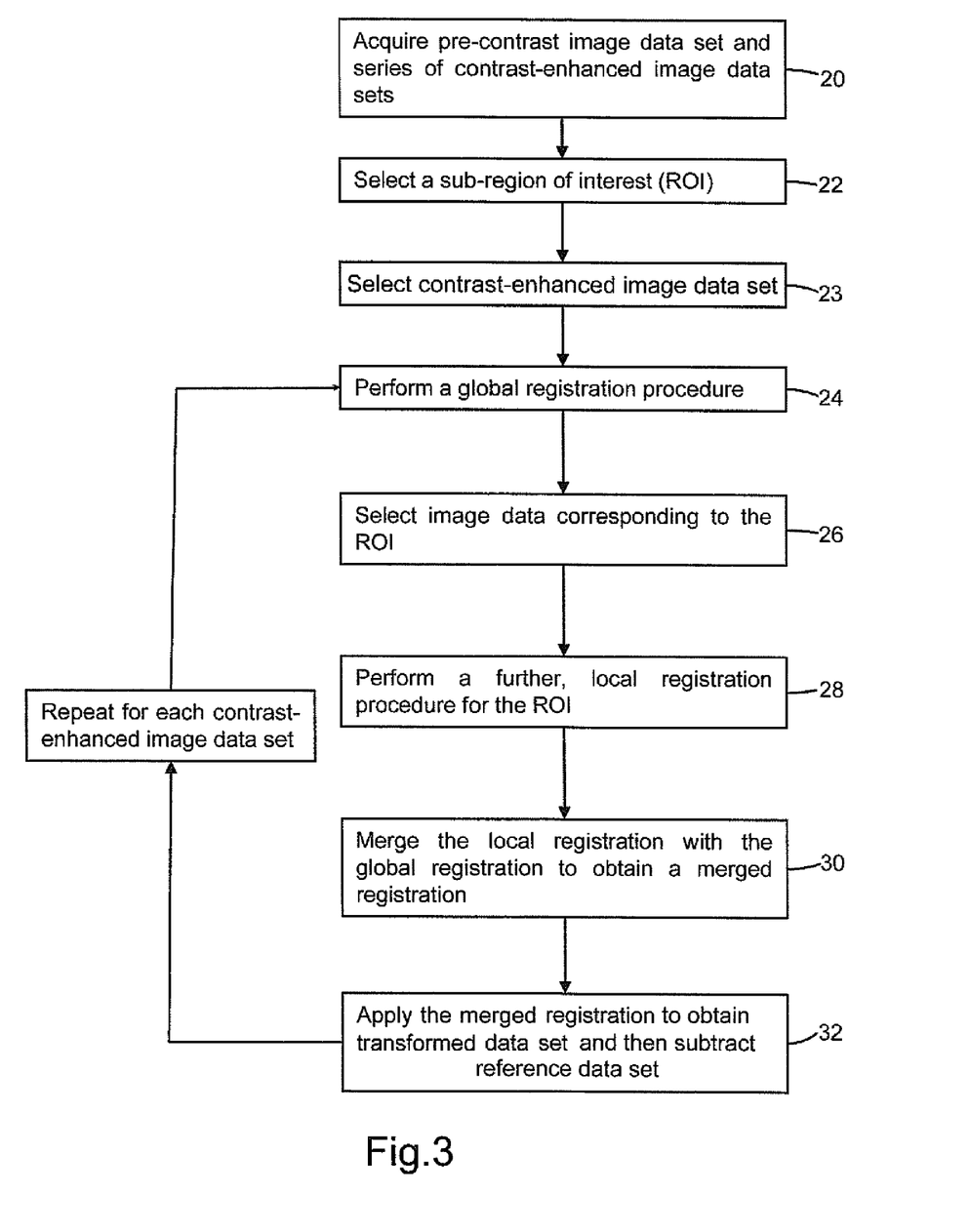
FIG. 3 is a flow chart illustrating in overview a mode of operation of the embodiment of FIG. 2
Figure 4A:
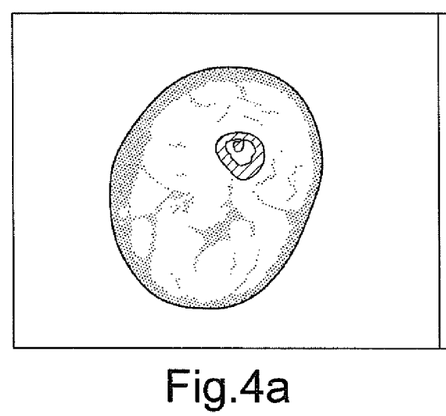
FIGS. 4a to 4f and 5a to 5f represent images that include selected sub-regions of interest.
Figure 4B:
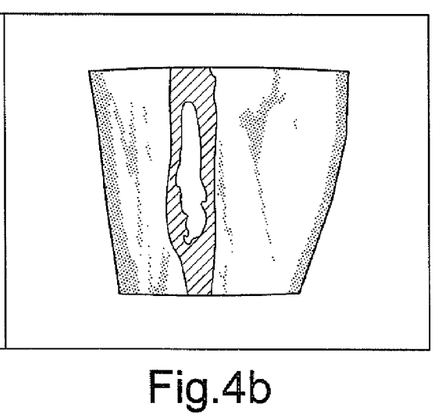
Figure 4C:
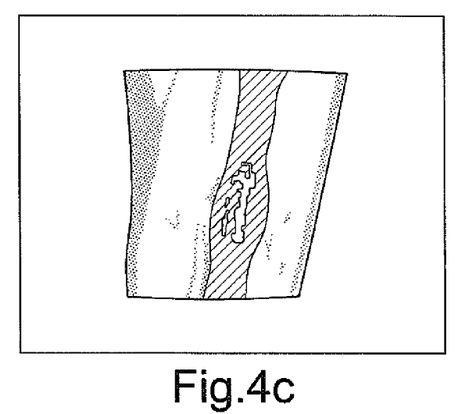
Figure 4D:
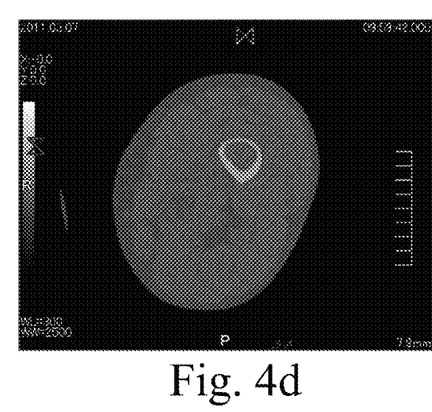
Figure 4E:
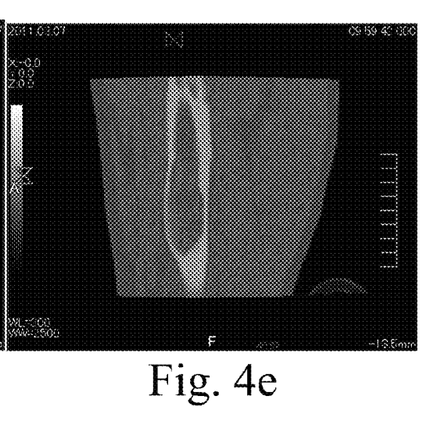
Figure 4F:
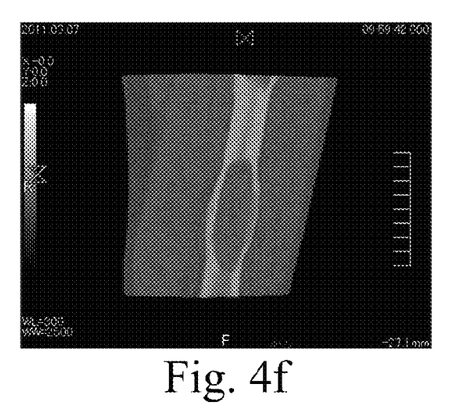
Figure 5A:
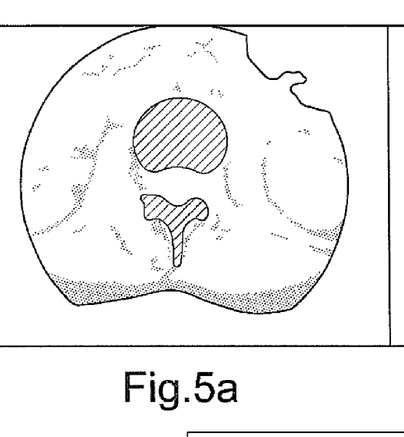
Figure 5B:
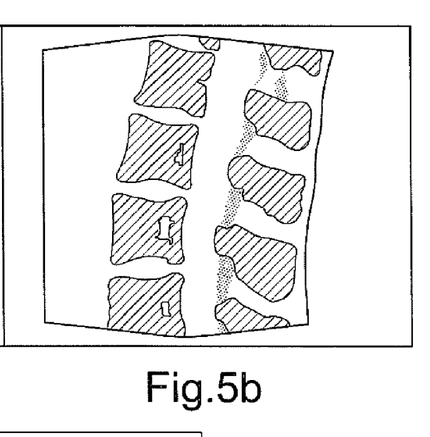
Figure 5C:
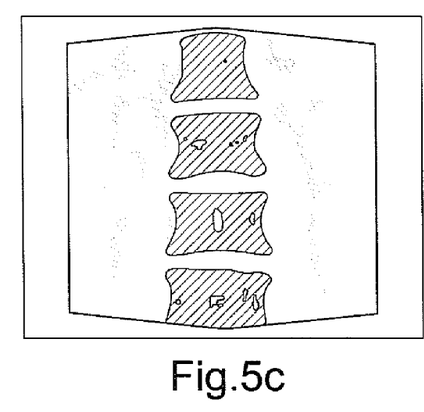
Figure 5D:
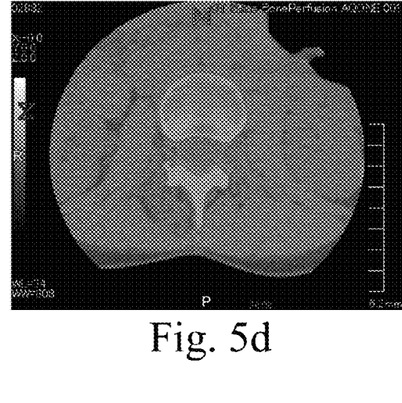
Figure 5E:
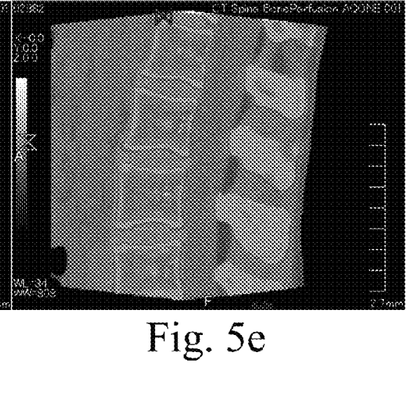
Figure 5F:
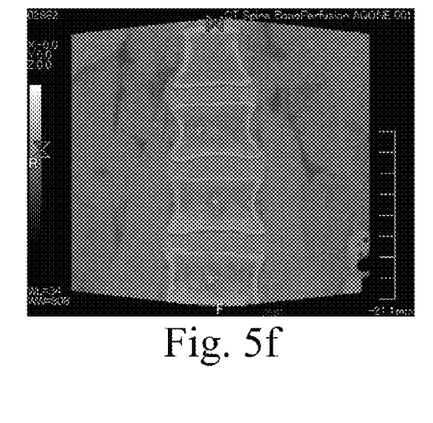

The system of FIG. 2 is configured to perform a process having a sequence of stages as illustrated in overview in the flow chart of FIG. 3.

At the first stage 20, the processing apparatus 2 acquires pre-contrast and contrast-enhanced image data sets from the scanner 6. In this example, the pre-contrast and contrast-enhanced image data sets show a region of a patient that includes a bone tumour within or adjacent to a vertebra of the patient. In other examples, the image data can represent any other region of a patient or other subject.

In the described example the series of contrast-enhanced image data sets comprises twenty image data sets each acquired at a respective acquisition time, and the period between successive acquisition times can vary between 5 and 20 seconds or more, depending on the scanning protocol. Thus, the series of contrast-enhanced image data sets can span a period of several minutes. That is sufficient time for a contrast agent, for example iodine, barium, gadolinium, or barium sulphate, to reach the tumour after being injected, to reach a maximum concentration in the tumour (also referred to as maximum perfusion) and to begin to decline.

It is likely that there will be at least some movement of the patient during the period of acquisition of the series of image data sets. It is a feature of the embodiment of FIG. 2 that it is able to automatically register the image data sets to a common reference so as to compensate for such movement.

At the next stage of the process 22, a sub-region of interest is selected automatically by the image selection unit 18. In the described example, the sub-region of interest comprises the bone where the tumour is present, and the selection process 22 comprises an automatic bone mask segmentation process. In alternative embodiments, any other type of automatic segmentation process may be performed by the image selection unit 18, for example a level set segmentation process or other segmentation process. Alternatively the sub-regions of interest may be selected manually by a user.

The automatic bone mask segmentation process is applied to the pre-contrast image data set, which is also referred to as the reference data set, in order to determine the sub-region or sub-regions of interest.

Firstly, a thresholding procedure is performed by the image selection unit to identify and select sub-regions that have an intensity greater than a predetermined threshold, for example, 200 Hounsfied Units (HU). The thresholding procedure comprises automatically determining one or more sub-regions of interest by comparing an intensity level of image data of the image data set or reference data set to a threshold and selecting the sub-region in dependence on the comparison.

Next, a morphological cleaning process is performed that discards those sub-regions having an intensity greater than the threshold but a size less than a predetermined threshold size (for example, a volume less than 1000 mm$^3$). The morphological cleaning process can be used to ensure that splinters of bone or calcification that are too small to be of clinical interest are not registered.

FIGS. 4*a* to 4*c*, and 5*a* to 5*c* are line drawings of selected sub-regions following the morphological cleaning process but before subsequent dilation and filling processes. The sub-regions are indicated using diagonal lines in the images. FIGS. 4*d* to 4*f* and 5*d* to 5*f* are the original scan images from which the line drawings of FIGS. 4*a* to 4*c* and 5*a* to 5*c* were obtained Next, as part of the determining of the sub-regions of interest by the image selection unit 18, a morphological filling process is performed on the remaining selected sub-regions. The image selection unit 18 determines a boundary of each sub-region and any gaps within the boundary of the sub-region are filled so that they are included with the sub-region, thus forming a mask for selecting data from the reference data set or from the series of sets of image data.

The morphological filling process can be performed with respect to the three-dimensional volume of the sub-region of interest, or with respect to two-dimensional slices through the sub-region. The morphological filling process can, for example, add the medullary cavity of bones to the sub-region of interest, and can ensure that the tissue within bones falls within the sub-region of interest. The morphological filling process can ensure that bone marrow and trabecular structures are not missed. It can be ensured that the sub-region of interest comprises at least one vessel or structure within which contrast agent perfuses.

A mask is then formed that represents the boundaries of the resulting sub-region or sub-regions of interest.

After the morphological cleaning and filling process, a morphological dilation process is performed in which the boundaries of the remaining selected sub-regions are expanded by a selected amount, for example by 10 mm in each direction. In later stages of the process of FIG. 3, all or part of the expanded part of each sub-region may be treated as a buffer region, as discussed in more detail below. The buffer region may form a halo around the actual bone area.

The dilation process can help to ensure that a sufficient amount of soft tissue is included in the sub-region that is subsequently registered. That can improve the results of the registration similarity metric (for example, Mutual Information) and therefore the registration results themselves. The use of a buffer region, formed by the dilation process, can help to seamlessly merge data from the region of interest with surrounding data in a transformed data set obtained in a later stage of the process (described in more detail below).

At the next part of the process, a series of processing steps is performed in respect of each of the contrast-enhanced image data sets in turn.

Beginning with a first one of the contrast-enhanced image data sets, which is selected at stage 23, a registration procedure is performed at stage 24 in which the reference data set (the non-contrast data set in this case) is registered to the contrast-enhanced data set. Suitable registration procedures are described in U.S. patent application Ser. No. 13/349,010 the entire content of which is hereby incorporated by reference.

In this case, a non-rigid registration procedure is applied to register the non-contrast data set to the contrast-enhanced data set by the registration unit 12. The non-rigid registration procedure is a global procedure that performs the registration with respect to substantially all of the data in the data sets or in a selected large region of the data sets.

A pre-processing stage may be used to eliminate extraneous data from the first and second image data sets before performing the global non-rigid registration procedure. The eliminated extraneous data can include, for example, data representative of air or gas, and in some cases may include data representative of padding or of a patient table or other artifact. The pre-processing stage may be omitted if desired.

Any suitable non-rigid registration procedure can be used at stage 24. In the embodiment of FIG. 2, the global non-rigid registration procedure uses Mutual Information as a similarity measure, and a non-rigid warpfield is computed based upon the Crum-Hills-Hawks scheme (William R. Crum, Derek L. G. Hill, David J. Hawkes. Information Theoretic Similarity Measures in Non-rigid Registration, Proceedings of IPMI '2003, pp. 378-387). One particular implementation is described in Piper et al. (J. Piper, Y. Ikeda, Y. Fujisawa, Y. Ohno, T. Yoshikawa, A. O'Neil, and I. Poole, Objective evaluation of the correction by non-rigid registration of abdominal organ motion in low-dose 4D dynamic contrast-enhanced CT, Physics in Medicine and Biology, February 2012).

A multiscale approach with subsampling factors 4 and 2 may be used, for example. This means that a global non-rigid registration at full scale, which has proven to be demanding from a runtime and memory point of view, is not performed in this mode of operation.

Each of the data sets comprise a set of voxels, each voxel comprising an intensity value and each voxel having a set of co-ordinates (for example, x, y, z co-ordinates) representing the spatial position for which the intensity value for that voxel was measured by the scanner 6 in a chosen co-ordinate system (for example, a cartesian co-ordinate system). The non-rigid registration generates a warpfield that comprises, for each voxel, an offset of the spatial co-ordinates for that voxel.

If the warpfield obtained from the non-rigid registration procedure is applied to the non-contrast data set in order to obtain a transformed non-contrast data set, the spatial co-ordinates of each voxel of the original non-contrast data set are shifted according to the warpfield such that a voxel in the non-contrast data set after transformation represents substantially the same position in the subject's body (substantially the same anatomical location) as a voxel in the contrast-enhanced data set having the same spatial co-ordinates.

In most practical circumstances it is necessary due to time or processing constraints to use a multi-scale registration procedure, in which reduced versions of the data sets are registered with each other. Such multi-scale registration procedures require interpolation of, and selection from, data points of the full data sets, and such interpolation and selection processes inevitably lead to some errors in the registration. The errors may be relatively small but can still have a significant effect in the assessment of small details of a diseased bone region.

The global registration operates on the whole volumes, or large parts of the volumes, and can bring tissues into approximate alignment. Given the subtractive nature of the application (discussed in more detail below) it is desired that the alignment in the sub-regions of interest (for example, within or near bones) is accurate. For this reason, a further refinement is performed only in the bone area or other sub-region of interest.

At the next stage 26 of the process, image data at positions within the boundary of the mask determined at stage 22 and defining the sub-region of interest (ROI) is selected. A further registration of the selected ROI pre-contrast data to the contrast enhanced data set is subsequently performed at stage 28 as will be described in more detail below. By performing a further registration of the data within the ROI it may be provided that the registration for that data can be improved, which may ultimately provide for improved perfusion analysis.

In the embodiment of FIG. 2, the ROI is the region over which a further, refined registration determined at the next stage 28 by the registration refinement unit 16 is applied fully. A buffer region surrounding the ROI (for example a shell beginning at the boundary of the ROI and extending by a predetermined distance in a radial direction) may also be defined as mentioned above. The further, refined registration is applied only partially over the buffer region as part of a merging procedure that merges the refined registration for the ROI with the global non-rigid registration. That merging is described in more detail below in connection with stage 30 of the procedure.

The further registration procedure is performed at stage 28 using the data corresponding to the ROI in order to refine the registration obtained for the ROI, and improve the quality of the registration.

The same registration algorithm may be used to perform the further; non-rigid registration as was used for the global, free-form registration at stage 24, but with different maximum resolution and with different internal algorithm parameters Alternatively the further registration of the ROI may be a free-form, non-rigid registration with a more detailed, i.e. smaller subsampling factor, e.g. 1, in some embodiments, in which case the warp field of the global registration is used as the starting point, without modification.

The data from the pre-contrast data set falling within the ROI are registered to the data from the contrast-enhanced data set.

There may be some pre-processing of the selected data prior to the performance of the local registration procedure in some modes of operation. For example, extraneous data such as data corresponding to padding, patient table or other equipment and/or air can be stripped out using known techniques before the local registration procedure is performed.

At the end of stage 28 a local registration is obtained that represents a registration of the pre-contrast data set to the contrast-enhanced data set at the ROI. A global non-rigid registration was already obtained at stage 24, that represents a registration of the entire non-contrast data set to the entire contrast enhanced data set. At the next stage, 30, the local registration is merged with the global non-rigid registration to obtain a merged registration.

The merging is performed by the registration refinement unit 16 using the buffer region surrounding the ROI (for example a hollow shell beginning at the boundary of the ROI and extending by a predetermined distance in a radial direction) that is defined by the image selection unit 18. The buffer region may be referred to as a feathering buffer or blending buffer and may be of a fixed size.

The merging can be performed using two successive processes. Firstly the local transformation and the global warpfield obtained from the global non-rigid registration are blended by taking the weighted average of the two at each location (each voxel) within the buffer, or by use of any other suitable combination process.

The weighting used in the weighted average calculation changes linearly with a change in distance from the ROI, resulting in only the local registration being used inside the ROI, and only the global non-rigid registration being used outside the blending buffer.

For a voxel having a location within the blending buffer but close to, the boundary with the ROI, the displacement of the voxel co-ordinates with respect to the co-ordinates of that voxel in the original image data set obtained according to the merged registration will be determined primarily by the local registration with a small adjustment due to the weighted global non-rigid registration. Similarly, for a voxel having a location within the blending buffer but close to the boundary furthest from the ROI, the displacement of the voxel co-ordinates with respect to the co-ordinates of that voxel in the original image data set obtained according to the merged registration will be determined primarily by the global non-rigid registration with a small adjustment due to the local registration.

Any other suitable merging processes can be used in alternative embodiments. For example, the weightings can vary in any suitable manner, and do not need to vary linearly with distance from the ROI. For example, the weightings can vary as any suitable function of distance, for instance as a quadratic or other polynomial function, a sigmoid function or a hyperbolic function of distance. The boundary between regions where weightings are applied and no weightings are applied can be selected in dependence on the difference between the global registration and the local registration for those locations, for example the size and location of the buffer region boundary can be determined automatically in dependence on such differences.

At the next stage, 32, the merged registration is applied to the non-contrast image data set to obtain a registered non-contrast image data set that is registered to the contrast enhanced image data set.

The registered non-contrast data set is then subtracted from the contrast enhanced image data set to obtain a subtracted data set that may exclude, or reduce, the prominence of features whose intensity does not vary with time, and that may display more clearly features, such as contrast-enhanced tissue, whose intensity does vary with time.

In some modes of operation, data representing material, such as air or gas, with intensity below a predetermined threshold is not subtracted, but is replaced in the subtracted data set by data having a uniform low value of intensity. That can produce subtraction results that may look more natural, or less distracting, to a user when displayed.

Next, a reverse transformation based on an inverse of the merged registration may be performed on the subtracted data set, also at stage 32.

The processes of stages 24 to 32 are then repeated: for each of the contrast enhanced image data sets. In each case, a global registration of the non-contrast data set to the contrast enhanced image data set is performed. A further, enhanced registration of the non-contrast data set to the contrast enhanced data set is then performed for the sub-region of interest, and the two registrations are merged to form a combined registration. The non-contrast data set is then transformed in accordance with the combined registration, and subtracted from the contrast enhanced data set. A reverse transformation is then performed on the resulting subtracted data set, if necessary.

Figure 6A:
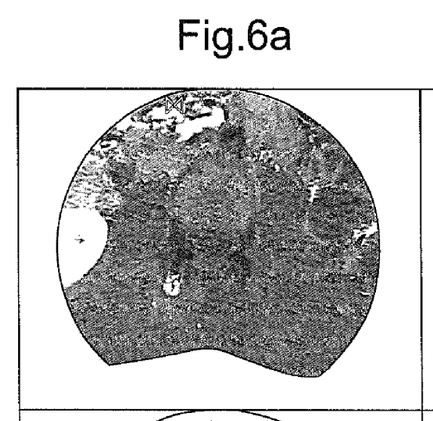
FIGS. 6 to 9 represent subtraction result images (upper rows) after registration and the contrast-enhanced original data sets (lower rows) of bone regions.
Figure 6B:
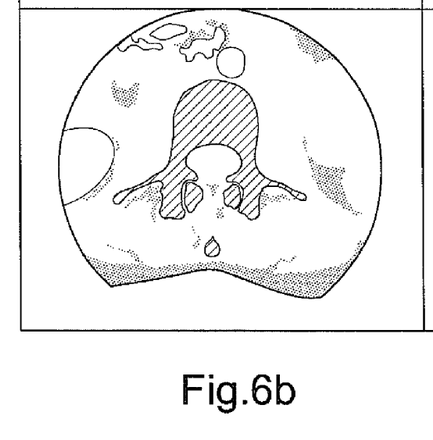
Figure 6C:
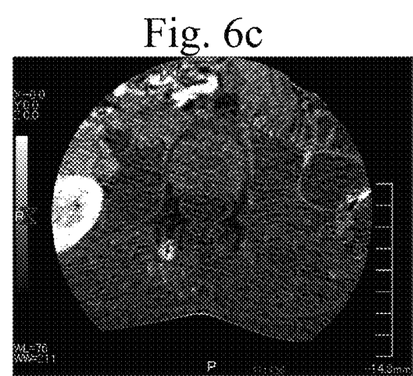
Figure 6D:
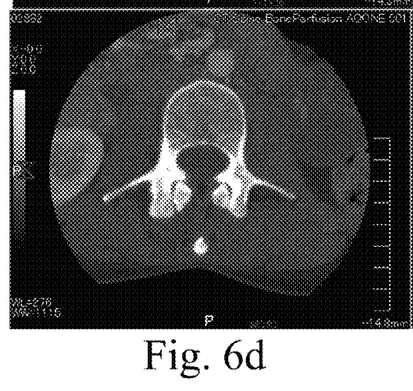
Figure 7A:
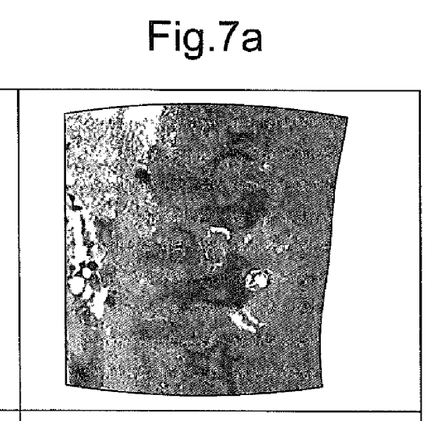
Figure 7B:
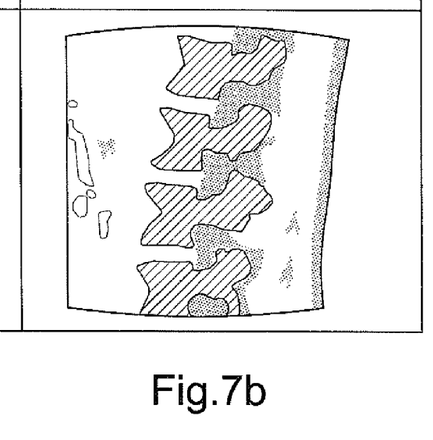
Figure 7C:
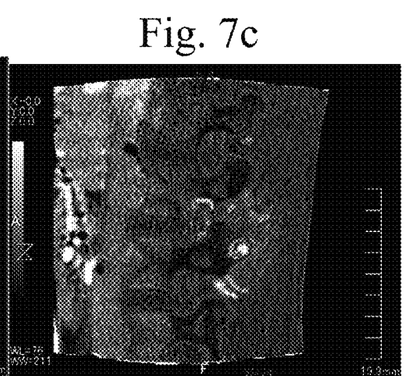
Figure 7D:
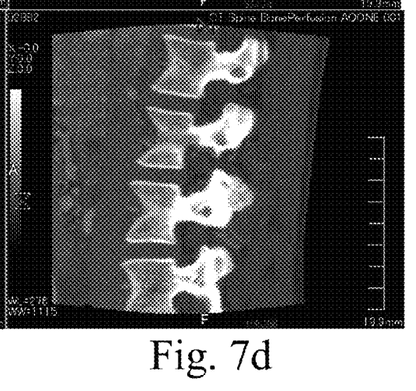

FIGS. 6b and 7b, are line drawings representing images of a bone region obtained from image data acquired in the presence of perfused contrast agent. FIGS. 6a and 7a are line drawings representing images of the same region following performance of registration and subtraction processes as described. FIGS. 6a and 6b represent a transversal view of the region, and FIGS. 7a and 7b represent a sagittal view of the region. FIGS. 6c, 6d, 7a and 7d are the original scan images from which the line drawings of FIGS. 6a, 6b, 7a and 7b were obtained.

Figure 8A:
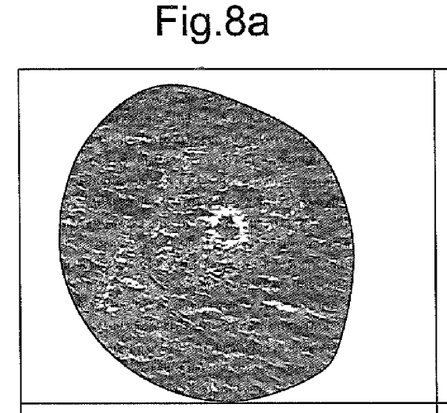
Figure 8B:
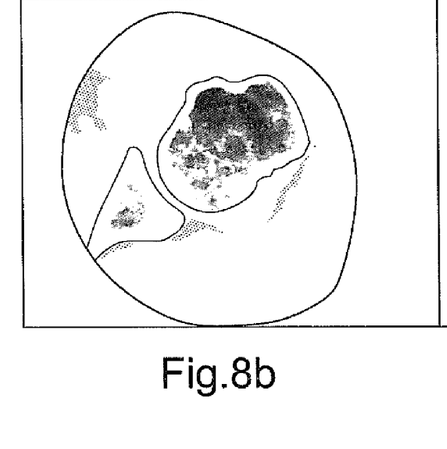
Figure 8C:
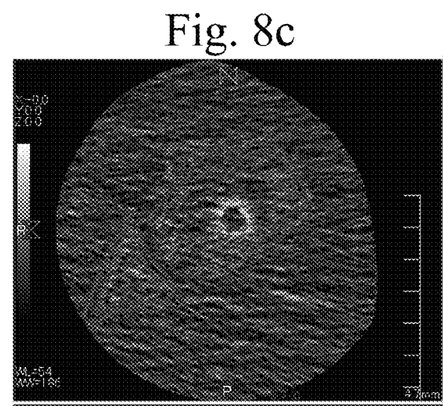
Figure 8D:
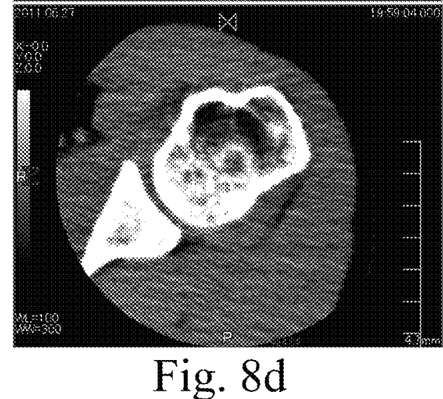
Figure 9A:
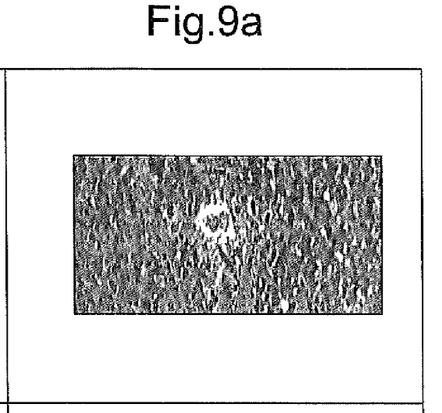
Figure 9B:
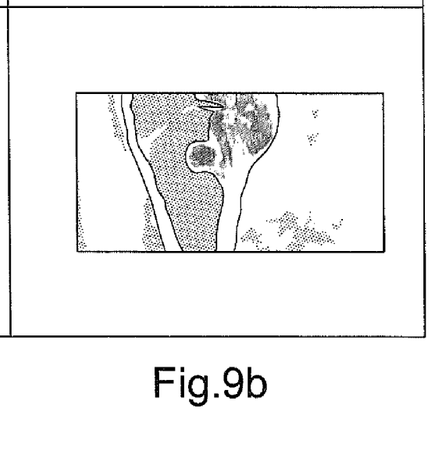
Figure 9C:
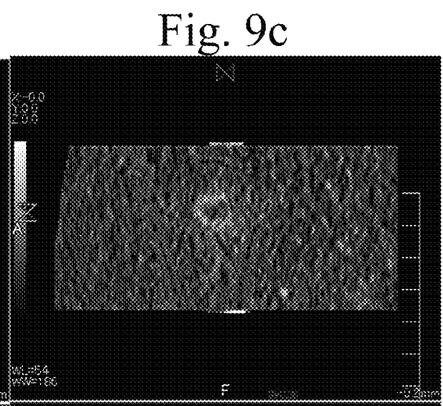
Figure 9D:
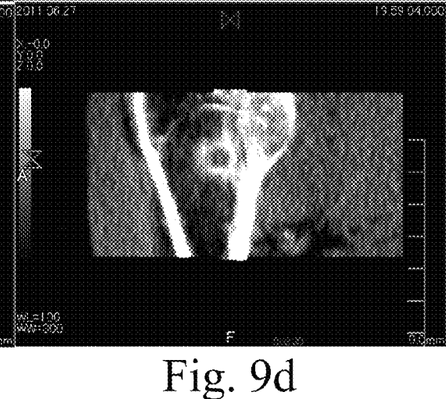

FIGS. 8b and 9b, are line drawings representing images of a further bone region obtained from image data acquired in the presence of perfused contrast agent. FIGS. 8a and 9a are line drawings representing images of the same region following performance of registration and subtraction processes as described. FIGS. 8a and 8b represent a transversal view of the region, and FIGS. 9a and 9b represent a sagittal view of the region. FIGS. 8c, 8d, 9a and 9d are the original scan images from which the line drawings of FIGS. 8a, 8b, 9a and 9b were obtained.

The registration and subtraction processes remove, or reduce the intensity of, bone and other features whose intensity do not vary with time.

By repeating the processes of the stages 24 to 32 for each of the contrast enhanced image data sets, a series of transformed subtracted data sets is obtained. Each of the transformed subtracted data sets is registered to a common reference, in this case the non-contrast data set, such that the same areas of anatomy appear in substantially the same position in each data set. Furthermore, features whose intensity does not vary with time are excluded, or their intensity is reduced, in the series of transformed subtracted data sets. Thus, all of the contrast enhanced phases of a dynamic diffusion sequence may be aligned automatically to provide a stabilised, motion-compensated, enhanced image sequence in which the perfusion of contrast agent into tissue can be viewed more clearly than in non-motion compensated and non-subtracted images.

Data within the sub-region of interest in the series of transformed subtracted data sets can subsequently be selected, and perfusion analysis can be performed on the selected data using any suitable perfusion analysis technique for quantification. As the transformed, subtracted data sets exclude, or reduce the intensity, of non-time varying features (such as surrounding bone) the perfusion analysis may be performed accurately. The embodiment is particularly useful for obtaining data for perfusion analysis in respect of bone tumours.

In the mode of operation of the embodiment of FIG. 2 described with reference to FIG. 3, the global registration is a free-form, non-rigid registration, and the local registration of the sub-region of interest is also a non-rigid registration in which a further free-form registration is applied to selected data corresponding to a ROI, and the resulting free-form registration is merged into the global free-form registration. In alternative modes of operation, any suitable combination of registrations can be used.

For example, in alternative modes of operation, the local registration procedure is an affine registration procedure. In still further embodiments, the local registration procedure may be a rigid registration procedure in which a rigid registration is applied to selected data corresponding to a ROI, and the resulting rigid registration is merged into the global free-form registration. Alternatively, the global registration can be a rigid or affine registration, and the local registration can be any one of a rigid, affine or free-form registration.

In other alternative modes of operation, there is a single registration only in respect of each contrast enhanced image data set (for example, either a rigid registration, an affine registration or a free-form registration). For instance, the registrations may be based on the sub-regions of interest only.

In some embodiments, a user is able to select the particular type or types of registration that are used.

In the mode of operation of the embodiment of FIG. 2 described with reference to FIG. 3, the non-contrast data set is registered to the contrast enhanced data set, and the non-contrast data set is transformed in accordance with the registration and the subtraction process is then performed.

In an alternative mode of operation, the contrast enhanced data set is registered to the non-contrast data set, and the contrast enhanced data set is transformed in accordance with the registration. In that mode of operation, there is no need to perform the reverse transformation at the end of the process, as each of the contrast enhanced data sets will be transformed to match the same reference data set (the non-contrast data set).

In a further alternative mode of operation, one of the series of contrast enhanced data sets is selected and is used as the reference data set. The procedure is then similar to that described with reference to FIG. 3, except that for each of the contrast enhanced data sets, the registration is performed with respect to the common, selected contrast enhanced data set rather than the non-contrast data set. The non-contrast data set (rather than the common selected contrast enhanced data set) is subtracted from each of the resulting transformed data sets. In that case, the common selected contrast enhanced data set may be referred to as the reference data set, and the non-contrast data set, used for the subtraction, may be referred to as a further reference data set.

Table 1 below summarises in overview registration and subsequent subtraction processes that may be performed in certain modes of operation, labelled A to F below, of an embodiment in which the series of sets of image data comprises N sets of image data obtained in the presence of contrast agent (referred to as Post1 ... PostN in the table) and a set of image data obtained before contrast agent was present (referred to as Pre in the table). In the Subtractions columns, the datasets mentioned are to be considered to be in their registered and transformed state as appropriate for the method. The modes of operation summarised Table 1 are non-limiting and are intended as illustrative examples only.

TABLE 1

|   | Registrations | Subtractions |
|---|---|---|
| A | Post1 to Pre, | Post1-Pre, |
|   | Post2 to Pre, | Post2-Pre, |
|   | ... | ... |
|   | PostN to Pre | PostN-Pre |
| B | Pre to Post1, | |
|   | Pre to Post2, | |
|   | ... | |
|   | Pre to PostN | |
| C | Pre to PostN, | |
|   | Post1 to PostN, | |
|   | ... | |
|   | Post(N − 1) to PostN | |
| D | Pre to Post1, | |
|   | Post1 to Post2, | |
|   | ... | |
|   | Post(N − 1) to PostN | |
| E | Pre to Post1, | As above, but apply inverse transformation to |
|   | Pre to Post2, | subtraction and registration results |
|   | ... | |
|   | Pre to PostN | |
| F | Pre to Post1, | Post1 - Pre, |
|   | Pre to Post2, | Post2 - Pre, |
|   | ... | ... |
|   | Pre to PostN | PostN - Pre |
|   |   | Post-process by global rigid |

In a mode of operation described in relation to FIG. 3, the registrations are performed in respect of the intensity data of the non-contrast data and the contrast enhanced data sets. In alternative modes of operation, the data sets are processed to obtain intensity gradient data, and the registration(s) are obtained with respect to the resulting intensity gradient data rather than the original intensity data. The intensity data is then transformed in accordance with the resulting registration in the same way as described in relation to FIG. 3.

The gradient magnitude as a function of position can be computed for the volume within the ROI for both pre- and post-contrast data (the first and second data sets in this case). The rigid registration process at stage 28 is then performed to register the gradient data obtained from the second data set to the gradient data obtained from the first data set.

In certain modes of operation, an image clamp is applied before calculating the gradient magnitudes, in order to focus only on structures of interest. Once the clamping has been performed the gradient magnitudes are calculated and the registration procedure of stage 28 is carried out. The resulting image data, after clamping and magnitude calculation is poorer in information, as much low and high intensity detail is lost, yet all the information is concentrated on the areas that it is most important to align correctly. It is important to note that usually the clamped gradient data is used only to obtain the correct registration. The registration is then applied to the intensity data of the non-contrast data set (or the contrast enhanced data set in some modes of operation) in order to transform that data set and thus align the data sets.

As mentioned above, various combinations of global and local registrations may be used in different embodiments. In some embodiments the global registration, or an approximation of the global registration, may be used as a starting point for the local registration procedure.

In embodiments in which the global registration and the local registration are both non-rigid registrations, the warp field obtained from the global registration can be used as the starting point for the local registration procedure. In some alternative embodiments, an approximation of the warpfield is obtained and that approximation is then used as the starting point for the local registration.

For instance, and by way of non-limiting example, in some embodiments the global registration is a non-rigid registration and the local registration is a rigid registration and in order to properly initialize the local rigid registration the warpfield inside the ROI is approximated by a rigid transformation, using the following method:

1. Sample point coordinates of voxels inside the ROI (for example, 20000 points)

2. For each point in the sample population, apply the warpfield and record the warped coordinates.

3. Using the resulting corresponding co-ordinate pairs (original voxel co-ordinates and corresponding warped coordinates), apply a multi-linear least square regression procedure to determine an affine transformation that maps the original voxel co-ordinates to the corresponding warped co-ordinates. This process returns an affine transformation matrix, which may still contain scaling and shearing components.

In order to remove the scaling and shearing components, the procedure continues as follows:—

4. Using polar decomposition, extract the rotational part of the affine transformation matrix using known techniques. An example of a suitable polar decomposition technique is described in K. Shoemake and T. Duff, Matrix Animation and Polar Decomposition, Proceedings of Graphical Interface 1992, pp 258-264, 1992.

5. Apply the affine transformation found in step 3 to the centre point of the ROI (also referred to as the centre of gravity of the ROI).

6. Determine the displacement between the warped and original centre of gravity, and take that displacement as representing the translational part of the rigid transformation.

7. Combine the results of steps 4, 5, and 6 to obtain the rigid approximation of the warpfield for the ROI. The rigid approximation comprises the rotational and translational components determined in steps 4 and 6. In this particular application scaling is fixed to one by design, so no extraction of the scaling is necessary. It is however possible also to extract the scaling component if desired.

At the end of process 7 a local rigid approximation of the non-rigid warpfield is obtained for the ROI. The local rigid approximation can only be as good as the original non-rigid registration, meaning that a poor global warpfield potentially will produce a poor local rigid approximation. In such a case, it is likely that the local rigid registration will fail. However, in practice it has been found that such situations do not occur and the global warpfields can generally be used to produce a satisfactory local rigid registration approximation.

The local rigid registration procedure then takes as a starting point the local rigid registration approximation, and then varies the registration using Powell-style optimization of the Mutual Information similarity measure, or any other suitable optimisation procedure, until an optimised local rigid registration is obtained.

Embodiments have been described in which image data representing bone has been automatically identified, for example based on intensity level (for example, CT number), and has been subtracted from time series of data sets, following registration and transformation processes. Features of interest that may be present within or close to the bone can then be viewed more clearly in the time series of data sets. However, the invention is not limited to automatically identifying sub-regions comprising bone. In certain embodiments, sub-regions comprising air, metal, soft tissue or other material as well as or instead of bone are automatically identified, for example based on intensity level. The image data representing such sub-regions may be subtracted from time series of data sets, following registration and transformation processes. Embodiments can be used to examine features of interest in any part of the human body or other subject.

It will be well understood by persons of ordinary skill in the art that whilst embodiments implement certain functionality by means of a computer program having computer-readable instructions that are executable to perform the method of the embodiments. The computer program functionality could be implemented in hardware (for example by means of CPU). However, the embodiments may also be implemented by one or more ASICs (application specific integrated circuit)) or by a mix of hardware and software.

Whilst particular units have been described herein, in alternative embodiments functionality of one or more of those units can be provided by a single unit, processing resource or other component, or functionality provided by a single unit can be provided by two or more units or other components in combination.

While certain embodiments have been described, these embodiments have been presented by way of example only, and are not intended to limit the scope of the inventions. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical image processing apparatus, comprising:
an image selection circuit that obtains a series of sets of image data, each set of image data representative of a region at a different time, and performs a segmentation process to segment a bone region as an anatomical feature in at least one of the sets of image data to determine a sub-region of interest comprising the anatomical feature;
a registration circuit that, for each set of image data of a plurality of the sets of image data in the series, performs a global registration process to obtain a global registration between a reference data set of the series and the set of image data; and
a registration refinement circuit that, for each set of image data of the plurality of sets of image data:
performs a local registration process, to obtain a local registration between the reference data set of the series and the set of image data within the sub-region of interest determined by the segmentation process;
obtains a combined registration based on the global registration and the local registration;
applies the combined registration to the reference data set or to the set of image data to obtain a transformed reference data set or transformed set of image data; and
performs at least one of (a), (b) and (c) to obtain a subtracted, transformed set of image data:
(a) subtracts the set of image data and the transformed reference data set;
(b) subtracts the transformed set of image data and the reference data set; and
(c) subtracts the transformed set of image data and a further reference data set.

2. An apparatus according to claim 1, wherein the performing of the segmentation process by the image selection circuit includes comparing an intensity level of image data of the image data set or of the reference data set to a threshold and determining the sub-region of interest according to the comparison.

3. An apparatus according to claim 2, wherein the intensity level is a CT number.

4. An apparatus according to claim 1, wherein the performing of the segmentation process by the image selection circuit includes performing a level set segmentation process or other segmentation process.

5. An apparatus according to claim 1, wherein the image selection circuit selects one of the sets of image data of the series to be the reference data set.

6. An apparatus according to claim 1, wherein at least one of:

(a) the reference data set comprises pre-contrast image data representative of the region; and (b) the plurality of sets of image data comprises contrast-enhanced image data.

7. An apparatus according to claim 1, wherein the reference data set is the same for each of the plurality of sets of image data of the series.

8. An apparatus according to claim 1, wherein the reference data set comprises a contrast-enhanced data set representative of the region.

9. An apparatus according to claim 1, wherein the reference data set is the same for each of the plurality of sets of image data, such that a motion-corrected sequence of subtracted images is obtained.

10. An apparatus according to claim 1, wherein
the series of sets of image data comprises a plurality of contrast-enhanced data sets and a non-contrast enhanced data set, and
the registration circuit subtracts the non-contrast enhanced data set, registered or otherwise, from each of the contrast-enhanced data sets, registered or otherwise.

11. An apparatus according to claim 1, wherein the registration circuit performs a reverse transformation.

12. An apparatus according to claim 1, wherein the performing of the local registration process comprises determining a starting point for the local registration from the global registration.

13. An apparatus according to claim 1, wherein the registration refinement circuit determines, for the sub-region of interest, a rigid approximation or an affine approximation of the global registration, and refines that approximation to determine the local registration for the sub-region of interest.

14. An apparatus according to claim 1, wherein
the sub-region of interest comprises, or is at least partially surrounded, by a buffer region, and
the combining by the registration refinement circuit comprises, for the buffer region, applying at least one weighting to one or both of the global registration and the local registration.

15. An apparatus according to claim 14, wherein the weighting or at least one of the weightings varies with distance from a central area of the sub-region of interest.

16. An apparatus according to claim 1, wherein the anatomical feature comprises bone.

17. An apparatus according to claim 1, wherein anatomical feature comprises at least one of a sign of pathology or at least one tumour.

18. An apparatus according to claim 1, wherein the determining of the sub-region of interest by the image selection circuit comprises determining a boundary of the sub-region of interest and filling in at least one gap within the boundary of the sub-region of interest to form a mask for selecting data from the reference data set or from the series of sets of image data.

19. An apparatus according to claim 1, wherein the determining of the sub-region of interest by the image selection circuit comprises determining a boundary of the sub-region of interest, and dilating the boundary of the sub-region of interest to form a mask for selecting data from the reference data set or from the plurality of sets of image data.

20. An apparatus according to claim 1, wherein the registration comprises at least one of:
a rigid registration;
an affine registration; and
a non-rigid registration.

21. An apparatus according to claim 1, wherein the medical image processing apparatus is further configured to perform perfusion analysis on the series of subtracted, transformed set of image data.

22. A method of medical image processing, comprising:
obtaining a series of sets of image data, each set of image data representative of a region at a different time;
determining, by circuitry, a sub-region of interest comprising an anatomical feature by performing a segmentation process to segment a bone region as the anatomical feature in at least one of the sets of image data; and
for each set of image data of a plurality of the sets of image data in the series:
performing, by the circuitry, a global registration process to obtain a global registration between a reference data set of the series and the set of image data;
performing, by the circuitry, a local registration process, to obtain a local registration between the reference data set of the series and the set of image data within the sub-region of interest;
obtaining, by the circuitry, a combined registration based on the global registration and the local registration;
applying, by the circuitry, the combined registration to the reference data set or to the set of image data to obtain a transformed reference data set or transformed set of image data; and
subtracting, by the circuitry, one of (a), (b) and (c) to obtain a subtracted, transformed set of image data:

(a) the set of image data and the transformed reference data set;

(b) the transformed set of image data and the reference data set; and (c) the transformed set of image data and a further reference data set.

23. A non-transitory computer readable medium storing computer-readable instructions that, when executed by a computer, cause the computer to perform the method according to claim 22.

* * * * *